United States Patent [19]
Yamada et al.

[11] 3,972,777
[45] Aug. 3, 1976

[54] METHOD FOR RECOVERY OF REFINED α-GALACTOSIDASE

[75] Inventors: Masaru Yamada, Kitami; Tsutomu Furuya, Tokyo; Chikashi Izumi, Kitami; Shigeyoshi Narita, Kitami; Hiroshi Ishikawa, Kitami, all of Japan

[73] Assignee: Hokkaido Sugar Co., Ltd., Tokyo, Japan

[22] Filed: Apr. 30, 1975

[21] Appl. No.: 572,944

[30] Foreign Application Priority Data
May 2, 1974 Japan.......................... 49-48747

[52] U.S. Cl............................................. 195/66 R
[51] Int. Cl.²......................................... C07G 7/028
[58] Field of Search........................... 195/66 R, 11

[56] References Cited
UNITED STATES PATENTS
3,623,955  11/1971  Keay ................................ 195/66 R
3,846,239  11/1974  Delente et al..................... 195/66 R OTHER PUBLICATIONS
Malhotra et al., Biochemische Zeitschrift 340, pp. 565–566 (1964).

Primary Examiner—Lionel M. Shapiro
Attorney, Agent, or Firm—Oblon, Fisher, Spivak, McClelland & Maier

[57] ABSTRACT

A method for the recovery of refined α-galactosidase is disclosed. This method comprises the steps of bringing an α-galactosidase-containing liquid into contact with a weakly acidic cation-exchange resin in the presence of a buffer solution for thereby allowing α-galactosidase to be selectively adsorbed by said resin, desorbing the adsorbed α-galactosidase from said resin by use of a buffer solution of a type such that at least one of the two factors, concentration and pH, has a higher value than that of the buffer solution used in said adsorption and thereafter recovering the desorbed α-galactosidase.

6 Claims, 1 Drawing Figure

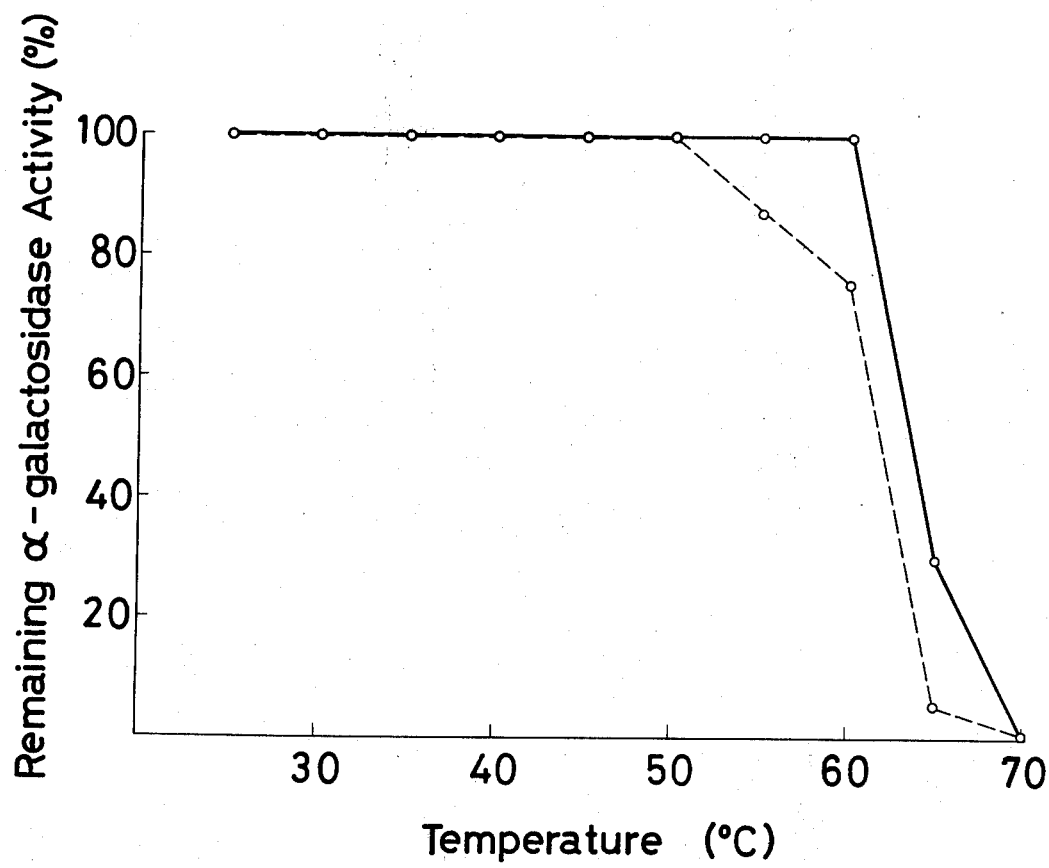

METHOD FOR RECOVERY OF REFINED α-GALACTOSIDASE

BACKGROUND OF THE INVENTION

This invention relates to a method for the recovery of refined α-galactosidase. More particularly, the present invention relates to a method for recovering α-galactosidase of high purity from an α-galactosidase-containing culture broth obtained by the culture of an α-galactosidase-producing microorganism or from an α-galactosidase-containing liquid obtained by the extraction of α-galactosidase from the microorganic cells after said culture.

Today it is known that α-galactosidase is produced by microorganisms such s actinomycetes, molds, etc. It is an enzyme which has the ability to hydrolyze raffinose into sucrose and glactose. In the beet sugar production industry, this enzyme is employed to hydrolyze the raffinose present in beet sugar solution such as beet juice and beet molasses so as to improve the yield of sucrose. Furthermore, α-galactosidase refined to high purity is used as a structure-determining agent in the chemical and biochemical fields.

α-Galactosidase has the ability to sever the α-galactoside linkage in saccharides. If α-galactosidase of high purity can be obtained inexpensively, therefore, it will possibly find utility in the production of foodstuffs, medicines and drugs, reagents, etc. as well as in the production of beet sugar and in the determination of structures of chemical compounds.

The α-galactosidase which is produced by the culture of a microorganism occurs chiefly within the cells of the microorganism. To obtain α-galactosidase of high purity from the microorganism, therefore, the produced enzyme must be extracted from the cells and then subjected to a refining treatment.

Heretofore, it has been known to effect the extraction of α-galactosidase by crushing the cells containing the formed α-galactosidase by physical means. By this method, however, the recovery ratio of α-galactosidase is on such a low order as 40 to 50% and the purity itself is not sufficiently high. It has further been known to extract the α-galactosidase from the microorganic cells and refine it by chemical methods such as by precipitation of α-galactosidase using ammonium sulfate, tannin or organic solvent. The extracts obtained by these methods, however, contain impurities such as extraneous proteins, sugars, nucleic acids, fats, etc. still in high concentrations, making it necessary to incorporate in the operation an extra process for purification. None of these methods, therefore, has been able to recover and refine α-galactosidase efficiently in one process.

An object of this invention is to provide a method for easily recoveing α-galactosidase of high purity at a high yield from the α-galactosidase-containing liquid.

SUMMARY OF THE INVENTION

To accomplish the object described above, the present invention provides a method which comprises bringing the α-galactosidase-containing liquid into contact with a weakly acidic cation-exchange resin in the presence of a buffer solution for thereby allowing the α-galactosidase to be selectively adsorbed by said resin and thereafter desorbing the adsorbed α-galactosidase from the resin by use of a buffer solution of which at least one of the two factors, concentration and pH, has a higher value than the buffer solution used in said adsorption.

Since the α-galactosidase present in the liquid is selectively adsorbed by the ion-exchange resin and thus can easily be separated from the mother liquid as described above, the method of this invention is notably simple as compared with the conventional refining methods, permits improvement of the yield and, furthermore, enjoys an advantage that the heat stability of the α-galactosidase refined by the present method is increased by approximately 10° Centigrade over that for the α-galactosidase refined by the conventional methods. Owing to such an increase in heat stability, the produced α-galactosidase can be used under a wider range of reaction conditions.

The other objects and other characteristic features of the present invention will become apparent from the description to be given in further detail herein below.

BRIEF EXPLANATION OF THE DRAWING

The drawing is a graph showing the heat stability of the enzyme refined by the method of this invention and that of the enzyme refined by the conventional method.

DETAILED DESCRIPTION OF THE INVENTION

The methods heretofore suggested for the refinement of α-galactosidase suffer from various disadvantages such as poor recovery ratio, insufficient purity and complication of operation. With a view to overcoming the difficulties, the inventors pursued various studies in search of a new method capable of advantageous recovery of α-galactosidase. They developed a hypothesis that recovery of α-galactosidase of high purity ought to be obtained easily by causing α-galactosidase to be selectively adsorbed by means of an ion-exchange resin capable of specifically combining the α-galactosidase. They tested ion-exchange resins to single out one which would qualify for the purpose. They have, consequently, made a discovery that the weakly acidic cation-exchange resin specifically provides adsorption of the α-galactosidase in the presence of a buffer solution under stated conditions and permits desorption thereof by use of a buffer solution satisfying a specific requirement. The present invention has been acomplished on the basis of this discovery. As the α-galactosidase-containing liquid to be subjected to the treatment by the method of this invention, there can be used either the α-galactosidase-containing culture broth obtained by culturing any of the known α-galactosidase-producing microorganisms or the α -galactosidase-containing liquid obtained by extracting the α-galactosidase contained in frozen microorganic cells or dry microorganic cells. The concentration of α-galactosidase in the broth or liquid makes little difference. Particularly in the case of the α-galactosidase which is formed by the culture of molds, since the enzyme occurs for the most part within the cells of the molds, the α-galactosidase is extracted from the cells by physically or chemical treating the cells. The extract consequently obtained is put to the treatment.

The ion-exchange resin to be used in the method of this invention is a weakly acidic cation-exchange resin of which examples are Amberlite IRC-50, IRC-75, IRC-84, CG-50 (products of Rohm and Hass company of the USA), Duolite CS-101, CS-100 (products of Diamond Alkali Co. of the USA), Permutit H-7 (product of the Permutit Co. of the USA), Ionac C-270 (product of American Zeolite Corp. of the USA), Wofatit CN (product of vabfarbfnfabriken Wolfen of the East-Germany), IMAC C-19 (product of Industrieele Maatschppij Activit N.V. of the Holland), Dowex CCR-2 (product of the Dow Chemical Co. of the USA), etc.

For the selective adsorption of α-galactosidase by said ion-exchange resin or for the desorption of the adsorbed α-galactosidase from said ion-exchange resin, there is used a buffer solution such as of phosphoric acid, acetic acid, sodium chloride or potassium chloride. The adsorption or desorption of the enzyme is closely related to the kind, concentration and pH status of the particular buffer solution to be used.

First, a description will be given of an example wherein the adsorption of α-galactosidase by the ion-exchange resin and the desorption of the adsorbed α-galactosidase from the resin were effected by use of phosphate buffer solutions.

Seven glass tubes were packed with an ion-exchange resin (Amberlite CG-50) and phosphate buffer solutions having a fixed concentration of 0.1 mol and adjusted to different pH values were passed through the ion-exchange resin beds in said glass tubes to equilibrate the ion-exchange resin. Thereafter, a 0.5-ml portion of α-galactosidase-containing liquid (total α-galactosidase activity 202,500 units) was introduced into each of the ion-exchange resin beds. The results of the α-galactosidase adsorption obtained were as shown in Table 1. The term "α-galactosidase activity" as used throughout the specification invariably refers to that which is determined by the PNPG process.

Then, a phosphate buffer solution having either a higher concentration or a higher pH value then the phosphate buffer solution used in said adsorption was passed through each ion-exchange resin bed which had adsorbed the α-galactosidase under the aforementioned conditions. The results of desorption obtained were as shown in Table 2. Part (A) of Table 2 shows the results of α-galactosidase desorption obtained by passing through the resin which had adsorbed the α-galactosidase under the conditions of Table 1, a phosphate buffer solution equal in pH value to the buffer solution used in said adsorption and differing therefrom in having a higher concentration of 0.2 mol. The results of α-galactosidase desorption obtained by treating the α-galactosidase-adsorbed resin with a phosphate buffer solution equal in concentration to the buffer solution used in said adsorption and differing therefrom solely because of an increased pH value of 9.2 are shown in Part (B) of Table 2. In the table, the adsorption ratios and the recovery ratios of α-galactosidase are both values calculated on the basis of the total α-galactosidase activity prior to adsorption treatment taken as 100.

Table 1

(Adsorption of α-galactosidase)

| Phosphate buffer soluton | Concentration(mol) P H | 0.1 4.5 | 0.1 5.3 | 0.1 5.9 | 0.1 6.5 | 0.1 7.0 | 0.1 8.0 | 0.1 9.2 |
|---|---|---|---|---|---|---|---|---|
| Amount of α-G adsorbed (units) | | 200,225 | 201,825 | 201,840 | 191,700 | 122,175 | 70,875 | 52,750 |
| Adsorption ratio of α-G (%) | | 99 | 100 | 100 | 95 | 61 | 35 | 27 |

Table 2 (A)

(Desorption of α-G)

| phosphate buffer solution | Concentration(mol) P H | 0.2 4.5 | 0.2 5.3 | 0.2 5.9 | 0.2 6.5 | 0.2 7.0 | 0.2 8.0 | 0.2 9.2 |
|---|---|---|---|---|---|---|---|---|
| ∓Amount of -G desorbed (units) | | 745 | 7,425 | 76,420 | 166,050 | 117,320 | 67,225 | 43,625 |
| Recovery ratio of α-G (%) | | 0.0 | 3 | 37 | 82 | 57 | 33 | 21 |

Table 2 (B)

| Phosphate buffer solution | Concentration(mol) P H | 0.2 9.2 | 0.2 9.2 | 0.2 9.2 | 0.2 9.2 | 0.2 9.2 | 0.2 9.2 | — |
|---|---|---|---|---|---|---|---|---|
| Amount of α-G desorbed (units) | | 199,800 | 184,275 | 128,925 | 8,775 | 675 | 670 | — |
| Recovery ratio of α-G (%) | | 97 | 94 | 63 | 4 | 0.0 | 0.0 | — |

It is clear from the foregoing tables that when the adsorption of α-galactosidase by the ion-exchange resin is attempted in the presence of a phosphate buffer solution of which the concentration is 0.1 mol, 95% or more of the whole α-galactosidase present is adsorbed by the resin insofar as the pH value falls in the range of from 4 to 6.5. In the desorption of the adsorbed α-galactosidase from the resin, if the adsorption has been effected under relatively low pH values of 4 to 6, there is a tendency for the desorption to be facilitated more by increasing the pH value of the buffer solution than by heightening the concentration thereof. If the adsorption has been carried out under relatively high pH values of 6 to 6.5, however, there is a tendency for the desorption to be facilitated more by increasing the concentration of the buffer solution than by heightening the pH value thereof.

The description will now be given of an experiment in which the adsorption of α-galactosidase by the ion-exchange resin and the desorption of the adsorbed α-galactosidase from the resin were effected by use of acetate buffer solutions.

Six glass tubes were packed with an ion-exchange resin (Amberlite CG-50) and acetate buffer solutions having different concentrations and adjusted to different pH values were passed through the ion-exchange resin beds in the glass tubes to equilibrate the ion-exchange resin. Thereafter, a 0.5-ml portion of α-galactosidase-containing liquid (total α-galactosidase activity 202,500 units) was introduced into each of the ion-exchange resin beds. The results of the α-galactosidase adsorption obtained were as shown in Table 3.

Parts (A), (B) and (C) of Table 4 show respectively the results of α-galactosidase desorption obtained by passing through the resin which had adsorbed α-galactosidase, an acetate buffer solution having a higher concentration or adjusted to a higher pH value than the acetate buffer solution used for said adsorption. Fist, the desorption was effected by using a buffer solution adjusted to the same pH value as the buffer solution used in said adsorption and having a higher concentration of 0.2 mol (Part (A)). Then, the desorption of the remaining adsorbed α-galactosidase from the resin was made by using a buffer solution having an even higher concentration of 1.0 mol (Part (B)). Finally, the desorption of still remaining α-galactosidase from the resin was tried by using an acetate buffer solution adjusted to pH 9.2 and having a concentration of 0.2 mol (Part (C)).

the presence of an acetate buffer solution of which the concentration is in the range of from 0.01 to 0.05 mol, 70% or more of the whole α-galactosidase present is adsorbed by the resin insofar as the pH value falls in the range of from 3.5 to 5, but that the adsorption ratio sharply declines if the pH value is increased beyond the upper limit of said range. It is noted that in the desorption of the adsorbed α-galactosidase from the resin, the desorption is facilitated more by heightening the pH value of the desorbing buffer solution than by increasing the concentration thereof as indicated in Table 4 if the preceding adsorption has been effected in the neighborhood of pH 4. If the adsorption has been effected in the neighborhood of pH 5, however, there is a tendency for the desorption of the adsorbed α-galactosidase to be facilitated more by increasing the concentration of the desorbing buffer solution than by heightening the pH value thereof. If the desorption of the adsorbed α-galactosidase is attempted by a buffer solution having a pH value in the range of from 6 to 9, practically 100% of the whole α-galactosidase adsorbed by the ion-exchange resin can be desorbed and recovered. As the pH value increases, however, those proteins other than α-galactosidase which have been adsorbed by the resin are desorbed to degrade the specific α-galactosidase activity (α-galactosidase activity per mg of proteins). Accordingly, α-galactosidase Table 3

(Adsorption of α-G)

| Acetate buffer solution | Concentration(mol) | 0.05 | 0.05 | 0.05 | 0.05 | 0.01 | 0.01 |
|---|---|---|---|---|---|---|---|
| | P H | 3.5 | 4.1 | 5.0 | 5.9 | 4.1 | 5.0 |
| Amount of α-G adsorbed (units) | | 178,925 | 201,505 | 201,875 | 18,200 | 141,750 | 200,950 |
| Adsorption ratio of α-G (%) | | 88.4 | 99.5 | 99.7 | 8.9 | 70.0 | 99.2 |

Table 4 (A)

(Desorption of α-G)

| Acetate buffer solution | Concentration(mol) | 0.2 | 0.2 | 0.2 | 0.2 | 0.2 | 0.2 |
|---|---|---|---|---|---|---|---|
| | P H | 3.5 | 4.1 | 5.0 | 5.9 | 4.1 | 5.0 |
| Amount of α-G desorbed (units) | | 620 | 620 | 705 | 10,700 | 825 | 2,100 |
| Recovery ratio of α-G (%) | | 0.0 | 0.0 | 0.0 | 5.3 | 0.0 | 0.1 |

Table 4 (B)

| Acetate buffer solution | Concentration(mol) | 1.0 | 1.0 | 1.0 | — | 1.0 | 1.0 |
|---|---|---|---|---|---|---|---|
| | P H | 3.5 | 4.1 | 5.0 | — | 4.1 | 5.0 |
| Amount of α-G desorbed (units) | | 675 | 620 | 202,250 | — | 650 | 199,475 |
| Recovery ratio of α-G | | 0.0 | 0.0 | 99.9 | — | 0.0 | 98.5 |

Table 4 (C)

| Acetate buffer solution | Concentration(mol) | 0.2 | 0.2 | 0.2 | — | 0.2 | 0.2 |
|---|---|---|---|---|---|---|---|
| | P H | 9.2 | 9.2 | 9.2 | — | 9.2 | 9.2 |
| Amount of α-G desorbed (units) | | 177,625 | 202,100 | 700 | — | 140,150 | 620 |
| Recovery ratio of α-G (%) | | 87.7 | 99.8 | 0.0 | — | 69.2 | 0.0 |

It is clear from Table 3 that when the adsorption of α-galactosidase by the ion-exchange resin is made in having a high specific activity can be obtained by using a buffer solution having a pH value of not more than 7 for the desorption of the adsorbed α-galactosidase.

When the adsorption of α-galactosidase by the ion-exchange resin and the desorption of the adsorbed α-galactosidase from the resin are attempted by use of a buffer solution of sodium chloride or potassium chloride, the adsorption indicates a tendency similar to that observed in the adsorption by use of a phosphate buffer solution. In the case of a chloride buffer solution adjusted to pH 5 and having a concentration of 0.05 mol, the adsorption ratio of α-galactosidase exceeds 90%. There is a tendency for the desorption to be facilitated more by heightening the pH value of the buffer solution than by increasing the concentration thereof.

The buffer solution to be used for adsorption is not required to be of the same kind as that which is used for desorption. For example, the α-galactosidase which has been adsorbed by the ion-exchange resin in the presence of an acetate buffer solution or a sodium chloride buffer solution may be desorbed by use of a phosphate buffer solution. Conversely, the α-galactosidase which has been adsorbed by the resin in the presence of a phosphate buffer solution may be desorbed by using an acetate buffer solution. In any event, it is essential that the buffer solution to be used for the desorption excel the buffer solution used for the adsorption in at least one of the factors, concentration and pH value. Otherwise, there can be obtained no sufficient desorption.

The temperature at which the adsorption of α-galactosidase by the ion-exchange resin or the desorption of the adsorbed α-galactosidase from said resin is carried out has no appreciable effect upon the recovery ratio. It is only required to be lower than the highest temperature at which the ion-exchange resin in use is stable and also lower than the inactivating temperature of the enzyme.

The adsorption of α-galactosidase and the desorption of the adsorbed α-galactosidase can be accomplished by using any of the various means known to the art. For example, a column is packed with the ion-exchange resin and the resin is equilibrated with the buffer solution. Thereafter, the α-galactosidase-containing liquid is introduced into the column so as to permit the α-galactosidase to be adsorbed by the ion-exchange resin.

Subsequently, the buffer solution for the desorption is passed through the bed of resin which has adsorbed the α-galactosidase, with the result that the adsorbed α-galactosidase is discharged from the resin bed in conjunction with the buffer solution. The α-galactosidase is then separated and recovered from the buffer solution by the known deionization method such as the semipermeable membrane (exosmotic pressure) method or the gel filtration method. The enzyme refined according to the present invention can be further purified by a known method for precipitation of α-galactosidase by using ammonium sulfate, tannin or organic solvent.

A horizontal reaction tank may be used in place of said column: The reaction tank is charged with the ion-exchange resin. Thereafter, the α-galactosidase-containing liquid and the buffer solution for adsorption are simultaneously passed through the resin bed so as to permit the α-galactosidase to be adsorbed by the resin. Then, the buffer solution for desorption may be passed to have the adsorbed α-galactosidase desorbed from the resin. Alternatively, there may be adopted a batchwise process: A container made of metallic gauze is filled with the ion-exchange resin. This vessel is then immersed and agitated in a reaction tank containing the α-galactosidase-containing liquid and the buffer solution for adsorption in order for the resin to contact and adsorb the α-galactosidase. Then, the container is lifted from the reaction tank and immersed in another reaction tank containing the buffer solution for desorption, so that the adsorbed α-galactosidase is desorbed from the resin by the buffer solution. In either event, better results are obtained when the ion-exchange resin is equilibrated in advance with the buffer solution intended for the adsorption.

As regards the treating time, a time long enough for the α-galactosidase-containing liquid or the buffer solution to pass through the ion-exchange resin bed will suffice for ample adsorption or desorption in the case of a column or a horizontal reaction tank. In the case of a batchwise operation, about 5 minutes of time will suffice for adsorption or for desorption. Any excess time given for the adsorption or desorption fails to provide any substantial enhancement of the adsorption ratio or recovery ratio.

As is evident from the foregoing description, the method of the present invention is unusually simple because it only requires proper adjustment of the concentration or pH value of the buffer solutions for the purpose of enabling the α-galactosidase to be adsorbed by the ion-exchange resin and the adsorbed α-galactosidase to be desorbed from the resin. Moreover, of the proteins adsorbed by the ion-exchange resin, those other than α-galactosidase are hardly desorbed from the resin, making it possible to obtain α-galactosidase in high purity. This trend is particularly conspicuous when acetate buffer solutions are employed for the operation.

Furthermore, the α-galactosidase which is refined by the method of this invention enjoys an improvement of about 10 Centigrade degrees in its heat stability. To be exact, while the α-galactosidase obtained by the conventional method becomes inactive as the temperature rises above the level of about 50°C, the α-galactosidase refined by the method of this invention is not inactivated until the temperature rises about 60°C. Such improvement in the heat stability warrants a proportional increase in the reaction temperature and enables the reaction to proceed with added stability against temperature, offering a decided advantage in the use of the refined α-galactosidase.

Heretofore there have been suggested many refining methods involving use of ion-exchange resins. However, virtually no method has so far been suggested which is developed to accomplish the adsorption and desorption of a strictly specific enzyme by use of an ion-exchange resin as contemplated by the present invention. When the ion-exchange resin is degraded in its adsorbability for α-galactosidase through continued service, it can then be regenerated by the known method. Thus, the ion-exchange resin can be used semi-permanently, making the operation highly economical.

The present invention will be described with reference to preferred embodiments herein below.

EXAMPLE 1

A glass tube 1 cm in diameter and 5 cm in length was packed with 3 g of an ion-exchange resin (Amberlite CG-50). Then, 0.1M phosphate buffer solution (pH 4.5) was passed through the glass tube to equilibrate the resin. To the resin, 0.5 ml of α-galactosidase-containing liquid (total α-galactosidase activity 202,500 units) was introduced at room temperature. Thereafter, 100 ml of said buffer solution was passed to elute free α-galactosidase, proteins other than α-galactosidase and other impurities.

The liquid consequently discharged from the glass tube was tested and found to contain 3,775 units of α-galactosidase activity, indicating that the adsorption ratio of α-galactosidase was about 98.1%.

Next 50 ml of 0.2M phosphate buffer solution (pH 9.2) was passed through said resin. The buffer solution which was consequently discharged from the glass tube was tested and shown to have 196,920 units of α-galactosidase activity, indicating that 99.1% of the whole α-galactosidase adsorbed on the ion-exchange resin was desorbed and further that the recovery ratio of α-galactosidase was about 97.2% based on the total α-galactosidase-activity of the α-galactosidase-containing liquid.

The adsorption and desorption steps were repeated in the manner as described above except that in place of 0.2M phosphate buffer solution of pH 9.2, 0.1M phosphate buffer solution of pH 9.2 was used as the solution for the desorption. In this case the solution which was discharged from the glass tube contained 149,820 units of α-galactosidase and the recovery ratio of α-galactosidase based on the initial total α-galactosidase activity was about 74%.

EXAMPLE 2

By following the procedure of Example 1, the ion-exchange resin in the glass tube was equilibrated by use of a 0.05M acetate buffer solution (pH 4.0). To the resin, 0.5 ml of α-galactosidase-containing liquid (total α-galactosidase activity 202,500 units) was introduced. Thereafter, the same buffer solution was passed through the resin to give it a washing. The liquid consequently discharged from the glass tube was tested and found to contain 620 units of α-galactosidase, indicating that the adsorption ratio of α-galactosidase was about 99.7%.

Next 0.2M acetate buffer solution (pH 6.0) was sent through the ion-exchange resin. The buffer solution which was consequently discharged from the glass tube was tested and found to have 194,290 units of α-galactosidase, indicating that 96.2% of the whole α-galactosidase adsorbed by the resin was desorbed from the resin and further that the recovery ratio was 95.5% based on the total α-galactosidase activity of the α-galactosidase-containing liquid introduced.

The procedure was faithfully repeated by using the buffer solution of the description given in Table 5 to effect adsorption and desorption of α-galactosidase. The results obtained were as shown in Table 5.

a 0.1M of acetate buffer solution (pH 4.1). To the resin, 0.5 ml of α-galactosidase-containing liquid (total α-galactosidase activity 202,500 units) was introduced. Thereafter, the same buffer solution as mentioned above was passed through the resin to wash it. The liquid consequently discharged from the glass tube contained 10,120 units of α-galactosidase, indicating that the adsorption ratio of α-galactosidase was about 99.7%.

Next, acetate buffer solution (pH 9.2) of the same concentration (0.1M) was introduced to the ion-exchange resin. The buffer solution which was consequently discharged from the glass tube was tested and found to contain 127,110 units of α-galactosidase, indicating that the recovery ratio was about 63% based on the total α-galactosidase activity of the α-galactosidase-containing liquid introduced.

EXAMPLE 4

As in the procedure of Example 1, an ion-exchange resin (Amberlite IRC-50) was equilibrated by using 0.1M phosphate buffer solution (pH 4.5). To the resin, 0.5 ml of an α-galactosidase-containing liquid (total α-galactosidase activity 202,500 units) was introduced. Thereafter, the resin was washed by using the same buffer solution. The liquid consequently discharged from the glass tube was tested and found to contain 35,100 units of α-galactosidase, indicating that the adsorption ratio of α-galactosidase was 85.1%.

Then, 0.2M phosphate buffer solution (pH 9.2) was passed through the resin. The buffer solution discharged from the glass tube was tested and shown to have 119,110 units of α-galactosidase activity, indicating that the recovery ratio of α-galactosidase was about 50.7% based on the total α-galactosidase activity.

When the procedure was repeated by using 0.05M acetate buffer solution (pH 5.0) for the adsorption and the same buffer solution also for the desorption, the adsorption ratio of α-galactosidase was found to be 95.2% (the discharge liquid containing 11,205 units of α-galactosidase activity) and the recovery ratio of α-galactosidase based on the initial total α-galactosidase activity to be 50.2% (the recovered α-galactosidase having 117,895 units).

EXAMPLE 5

By following the procedure of Example 1, 3 g of an ion-exchange resin (Amberlite CG-50) was equilibrated by using 0.05M acetate buffer solution (pH 5.0). To this resin, 0.5 ml of α-galactosidase-containing liquid (total α-galactosidase activity 235,000 units, specific activity 42,000 units/mg of protein) was intro- Table 5

| Buffer solution for adsorption | Amount of α-G adsorbed (units) | Adsorption ratio of α-G (%) | Buffer solution for desorption | Amount of α-G desorbed (units) | Recovery ratio of α-G (%) |
|---|---|---|---|---|---|
| 0.05M acetate buffer solution (PH 5.0) | 201,575 | 99.5 | 0.5M acetate buffer solution (PH 5.0) | 193,485 | 95.5 |
| 0.05M potassium chloride buffer solution (PH 5.0) | 188,750 | 93.2 | 0.2M sulfate buffer solution (PH 9.2) | 180,225 | 89.0 |

EXAMPLE 3

By following the procedure of Example 1, the ion-exchange resin in the glass tube was equilibrated by use of duced. Thereafter, the resin was washed with the same buffer solution. The liquid thus discharged was tested and found to contain 625 units of α-galactosidase activity, indicating that the adsorption ratio of α-galactosidase was nearly 100%.

The procedure was repeated by using the buffer solutions of the description given in Table 6 to find desorbed α-galactosidase activity, protein desorption and specific activity. The results were as shown in Table 6.

Table 6

| Phosphate solution for desorption | Amount of α-G desorbed (units) | Recovery ratio of α-G (%) | Amount of protein (mg) | Specific activity (units/mg) | Increase of specific activity (with initial value taken as unity) |
|---|---|---|---|---|---|
| 0.2M acetate buffer solution (PH 5.9) | 232,000 | 98.7 | 1.00 | 232,000 | 5.52 |
| 0.2M sulfate buffer solution (PH 5.9) | 99,000 | 42.1 | 0.53 | 187,000 | 4.45 |
| 0.2M sulfate buffer solution (PH 6.5) | 214,000 | 91.1 | 1.03 | 207,000 | 4.93 |
| 0.2M sulfate buffer solution (PH 7.0) | 227,000 | 96.6 | 1.42 | 160,000 | 3.81 |
| 0.2M sulfate buffer solution (PH 9.2) | 230,000 | 97.9 | 1.58 | 146,000 | 3.48 |

It is evident from Table 6 that the specific activity of the α-galactosidase rose several times, indicating that the enzyme was refined to high purity.

EXAMPLE 6

A vessel was charged with 5.0 ml of an α-galactosidase-containing liquid (total α-galactosidase activity 8,425,000 units, specific activity 132,000/mg), 5 ml of 1M phosphate buffer solution (pH 4.5), 40 ml of water and 5 g of an ion-exchange resin (Amberlite CG-50). The contents were agitated at 30°C for 20 minutes. Thereafter, the resin was washed with 0.1M phosphate buffer solution (pH 4.5). The amount of α-galactosidase adsorbed was 7,995,000 units, indicating that the adsorption ratio was 94.9%. The resin was immersed in 50 ml of 0.2M phosphate buffer solution having a pH value of 6.5 in one test run and 9.2 in the other test run to effect desorption of the adsorbed α-galactosidase. The results were as shown in Table 7.

Table 7

| PH value of buffer solution | Amount of α-G desorbed (units) | Recovery ratio of α-G (%) | Amount of protein (mg) | Specific activity (units/mg) |
|---|---|---|---|---|
| 6.5 | 7,276,000 | 86.4 | 24.17 | 301,000 |
| 9.2 | 7,618,000 | 90.4 | 35.26 | 216,000 |

The procedure described above was repeated under the same conditions, except the time adsorption treatment was varied. The results were as shown in Table 8.

Table 8

| Reaction time (min.) | 1 | 3 | 5 | 10 | 20 | 40 | 60 |
|---|---|---|---|---|---|---|---|
| Adsorption ratio of α-G (%) | 44.6 | 72.5 | 81.5 | 89.1 | 94.9 | 95.1 | 95.1 |
| Adsorption ratio of protein (%) | 37.5 | 48.2 | 50.6 | 53.6 | 54.2 | 56.5 | 56.1 |

It is seen from Table 8 that even in the batchwise operation, the adsorption ratio of α-galactosidase exceeds 80% when the adsorption treatment is given for a period of about 5 minutes.

EXAMPLE 7:

Similarly to the procedure of Example 6, a vessel was charged with 1.0 ml of an α-galactosidase-containing liquid (total α-galactosidase activity 1,685,000 units specific activity 132,000/mg), 0.5 ml of 1M potassium chloride (pH 5.0), 8.5 ml of water and 1 g of an ion-exchange resin (Amberlite CG-50). The contents were agitated at 30°C for 30 minutes. Thereafter, the resin was washed with 0.1M potassium chloride buffer solution. This resin was immersed in 0.2M phosphate buffer solution (pH 9.2) to effect desorption of α-galactosidase. By repeating the procedure, adsorption of α-galactosidase was accomplished by using 0.1M potassium chloride buffer solution, 0.05M and 0.1M sodium chloride buffer solutions. The resin which had adsorbed α-galactosidase was treated by using the same phosphate buffer solution to desorb the adsorbed α-galactosidase. The results were as shown in Table 9.

Table 9

| Kind of buffer solution | Concentration (mol) | Amount of α-G adsorbed (units) | Adsorption ratio of α-G (%) | Amount of α-G desorbed (units) | Recovery ratio of α-G (%) | Amount of protein (mg) | Specific activity (units/mg) |
|---|---|---|---|---|---|---|---|
| Potassium chloride buffer solution | 0.05 | 1,580,000 | 93.8 | 1,527,000 | 90.6 | 6.10 | 250,000 |
| | 0.1 | 1,548,000 | 91.9 | 1,449,000 | 86.0 | 6.31 | 230,000 |
| Sodium chloride buffer solution | 0.05 | 1,535,000 | 91.1 | 1,412,000 | 83.8 | 6.17 | 229,000 |
| | 0.1 | 1,506,000 | 89.4 | 1,387,000 | 82.3 | 6.07 | 229,000 |

EXAMPLE 8

A vessel was charged with 1.0 ml of an α-galactosidase-containing liquid (total activity 1,685,000 units), 1.0 ml of 1M phosphate buffer solution and 8.0 ml of water and a different amount (0.1 g, 0.25 g, 0.5 g, 0.75 g or 1.0 g) of an ion-exchange resin (Amberlite CG-50). The contents were agitated at 30°C for 60 minutes. The α-galactosidase adsorption ratios of the proteins adsorption ratios found were as shown in Table 10.

Table 10

| Amount of resin added | 0.1 | 0.25 | 0.5 | 0.75 | 1.0 |
|---|---|---|---|---|---|
| Adsorption ratio of α-G (%) | 26.0 | 48.8 | 72.7 | 90.0 | 91.6 |
| Adsorption ratio of proteins (%) | 28.6 | 36.3 | 44.6 | 54.2 | 57.1 |

It is clear from Table 10 that the amount of ion-exchange resin sufficient for the adsorption is 1 g per 2,300,000 units of α-galactosidase activity.

EXAMPLE 9

The procedure of Example 8 was repeated by using the same α-galactosidase-containing liquid and phosphate buffer solution and fixing the amount of resin at 1 g, except the agitation was given for 20 minutes at a different temperature (5°C, 20°C or 30°C). The amounts of α-galactosidase adsorbed and the adsorption ratios found were as shown in Table 11.

Table 11

| Temperature (°C) | 5 | 20 | 30 |
|---|---|---|---|
| Amount of α-G adsorbed (units) | 1,589,000 | 1,530,000 | 1,575,000 |
| Adsorption ratio of α-G (%) | 94.3 | 90.8 | 93.5 |

It is seen from Table 11 that the level of adsorption of α-galactosidase on the ion-exchange resin remains substantially consistent even when the treating temperature is different to some extent.

EXAMPLE 10

To 3,000 ml of an aqueous 0.1M NaCl solution (pH 9.0), 500 g of α-galactosidase-containing mold cells (total α-galactosidase activity 743,000,000 units) was added. The mixture was agitated at about 45°C for 4 hours, with the pH value maintained in the range of from 8.5 to 9.0, to extract α-galactosidase from the cells.

The extract thus obtained was filtered with gauze to remove the cells. The filtrate was adjusted with 2N sulfuric acid to pH 5.0, left to stand for about 3 hours to induce precipitation and centrifuged to remove the precipitate. In the resultant supernatant, 2,600 ml in volume, the total α-galactosidase activity was found to be 370,000,000 units.

To one half (1,300 ml) of the supernatant, potassium phosphate was added until the concentration was brought to 0.1M and the pH value to 4.5. Then, the resultant solution was passed through a column packed with 90 g of an ion-exchange resin (Amberlite CG-50) which had been equilibrated in advance with 0.1M potassium phosphate solution pH 4.5. Then, 500 ml of 0.2M disodium phosphate solution (pH 9.0) was introduced into said column. The liquid consequently discharged from the column was found to contain 175,650,000 units of α-galactosidase activity meaning that 94.9% of the α-galactosidase of the supernatant recovered.

To the remaining one half (1,300 ml) of the supernatant, ammonium sulfate was added until the final concentration was brought to 0.8 saturation without going through the treatment for adsorption and desorption by use of the ion-exchange resin described above. Thereafter, the solution was left to stand at about 5°C overnight to permit precipitation to ensue. The formed precipitate was filtered out with Celite (kieselguhr). The precipitate deposited on the Celite was dissolved together with the Celite in 0.1M phosphate buffer solution (pH 7.0). The solution was deprived of undissolved Celite by use of a glass filter. The filtrate thus obtained was found to contain 123,750,000 units of α-galactosidase activity meaning that 66.9% of the α-galactosidase was recovered. Accordingly, the yield of enzyme refined by the former procedure was much higher than the yield of enzyme refined by the latter procedure.

Further comparison of the two enzymes in terms of heat stability shows, as illustrated in the graph of the drawing, that both enzymes remained active up to 50°C and that about 12% of the latter enzyme was inactivated after standing at 55°C for 15 minutes and about 25% of said enzyme was inactivated up to 60°C for 15 minutes (dotted line in the drawing) while the former enzyme was hardly inactivated up to 60°C and was inactivated above 60°C (continuous line). According to the method of the present invention, the heat stability is improved by about 10°C possibly because the treatment with the ion-exchange resin changes the quality of α-galactosidase.

What is claimed is:

1. A method for recovering refined α-galactosidase from a liquid which is an extract of α-galactosidase containing microorganic cells or is an α-galactosidase culture broth, the liquid being in admixture with the cell material of the α-galactosidase producing microorganism, which consists essentially in the steps of filtration to remove the microorganic cell material, pH adjustment and precipitate removal, followed by the steps of bringing the resulting α-galactosidase-containing liquid into contact with a weakly acidic cation-exchange resin in the presence of a buffer solution (A) thereby causing the α-galactosidase in said liquid to be adsorbed by said resin, desorbing the adsorbed α-galactosidase from the resin by use of a buffer solution, (B), of which at least one of the factors, concentration and pH value, is higher than that of the buffer solution (A) used in said adsorption, and recovering the desorbed α-galactosidase in the liquid discharged from said resin.

2. The method for recovering refined α-galactosidase according to claim 1, wherein the buffer solution for adsorption is one member selected from the group consisting of phosphate buffer solution, acetate buffer solution, sodium chloride buffer solution and potassium chloride buffer solution, and the buffer solution for desorption is one member selected from the group consisting of phosphate buffer solution, acetate buffer solution, sodium chloride buffer solution and potassium chloride buffer solution.

3. The method according to claim 2, wherein α-galactosidase is adsorbed by the resin in the presence of 0.1M phosphate buffer solution of pH 4.5 – 7.0 and the adsorbed α-galactosidase is desorbed from the resin by use of 0.2M phosphate buffer solution of pH 4.5 – 7.0.

4. The method according to claim 2, wherein α-galactosidase is adsorbed by said resin in the presence of 0.5M acetate buffer solution of pH 3.5 – 5.0 and the adsorbed α-galactosidase is desorbed from the resin by use of 0.2M acetate buffer solution of pH 9.2.

5. The method according to claim 2, wherein α-galactosidase is adsorbed by said resin in the presence of 0.05M acetate buffer solution of pH 3.5 – 5.0 and the adsorbed α-galactosidase is desorbed from the resin by use of 1M acetate buffer solution of pH 5.0 – 9.2.

6. The method according to claim 2, wherein α-galactosidase is adsorbed by said resin in the presence of 0.05M acetate buffer solution of pH 3.5 – 5.0 and the adsorbed α-galactosidase is desorbed from the resin by use of 0.2M phosphate buffer solution of pH 6.5 – 9.2.

* * * * *